United States Patent
Brueckner et al.

(10) Patent No.: US 9,421,328 B2
(45) Date of Patent: Aug. 23, 2016

(54) CLOT TRAP, EXTERNAL FUNCTIONAL MEANS, BLOOD CIRCUIT AND TREATMENT APPARATUS

(75) Inventors: Christoph Brueckner, Geldersheim (DE); Martin Lauer, St. Wendel (DE); Manfred Weis, Ringstrasse (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 884 days.

(21) Appl. No.: 12/765,154

(22) Filed: Apr. 22, 2010

(65) Prior Publication Data

US 2010/0270230 A1    Oct. 28, 2010

Related U.S. Application Data

(60) Provisional application No. 61/185,623, filed on Jun. 10, 2009.

(30) Foreign Application Priority Data

Apr. 23, 2009  (DE) .......................... 10 2009 018664
Jun. 10, 2009  (DE) .......................... 10 2009 024 495

(51) Int. Cl.
| | |
|---|---|
| *B01D 29/01* | (2006.01) |
| *B01D 35/02* | (2006.01) |
| *B01D 36/00* | (2006.01) |
| *A61M 1/36* | (2006.01) |
| *A61M 5/165* | (2006.01) |

(52) U.S. Cl.
CPC ............. *A61M 5/165* (2013.01); *A61M 1/3627* (2013.01); *A61M 2205/125* (2013.01)

(58) Field of Classification Search
None
See application file for complete search history.

(56) References Cited

U.S. PATENT DOCUMENTS

| | | | |
|---|---|---|---|
| 4,806,135 A | | 2/1989 | Siposs |
| 4,985,153 A | * | 1/1991 | Kuroda et al. ................ 210/782 |
| 5,120,302 A | | 6/1992 | Vescovini et al. |
| 5,417,650 A | | 5/1995 | Gordon |
| 5,489,385 A | * | 2/1996 | Raabe et al. .................. 210/448 |
| 5,783,072 A | * | 7/1998 | Kenley et al. ............... 210/195.2 |
| 5,798,041 A | * | 8/1998 | Zuk, Jr. ......................... 210/456 |
| 6,458,278 B1 | * | 10/2002 | Leoncavallo et al. ......... 210/650 |
| 6,468,225 B1 | | 10/2002 | Lundgren |
| 6,491,656 B1 | | 12/2002 | Morris |
| 6,695,803 B1 | * | 2/2004 | Robinson et al. ............ 604/4.01 |
| 6,723,062 B1 | * | 4/2004 | Westberg et al. ............ 604/4.01 |
| 6,949,214 B2 | | 9/2005 | Frey |
| 2002/0026212 A1 | * | 2/2002 | Wholey et al. ................ 606/200 |
| 2002/0188276 A1 | * | 12/2002 | Evans et al. .................. 604/509 |

(Continued)

FOREIGN PATENT DOCUMENTS

| | | |
|---|---|---|
| DE | 3237016 A1 | 5/1983 |
| DE | 44 04 277 A1 | 8/1995 |

(Continued)

OTHER PUBLICATIONS

International Search Report from PCT/EP2010/002297 mailed on Jul. 27, 2010.

*Primary Examiner* — Dirk Bass
(74) *Attorney, Agent, or Firm* — Kenyon & Kenyon LLP (57) ABSTRACT

The present invention relates to a clot trap that comprises a disc-shaped screen surface for collecting clots in a fluid flowing through the screen surface. It further relates to an external blood cassette and a blood circuit, as well as a treatment apparatus.

20 Claims, 8 Drawing Sheets

(56) References Cited

U.S. PATENT DOCUMENTS

| | | |
|---|---|---|
| 2004/0127840 A1 | 7/2004 | Gara et al. |
| 2005/0021075 A1* | 1/2005 | Bonnette et al. ............. 606/200 |
| 2005/0139532 A1 | 6/2005 | Hershberger et al. |
| 2005/0191620 A1 | 9/2005 | McDevitt et al. |
| 2006/0189937 A1* | 8/2006 | Miner ........................ 604/122 |
| 2010/0200486 A1 | 8/2010 | Gunther et al. |

FOREIGN PATENT DOCUMENTS

| | | |
|---|---|---|
| DE | 297 06 807 U1 | 6/1997 |
| DE | 10304365 A1 | 8/2004 |
| DE | 10 2007 042 964 A1 | 3/2009 |
| DE | 10 2009 018664.6 A1 | 10/2010 |
| DE | 10 2009 024468.9 A1 | 12/2010 |
| EP | 0614675 A1 | 9/1994 |
| EP | 0758551 A1 | 2/1997 |
| GB | 2110564 A | 6/1983 |
| JP | 61247464 A | 11/1986 |
| JP | 6292723 A | 10/1994 |
| JP | 08-509991 A | 10/1996 |
| JP | 2001-009212 A | 1/2001 |
| JP | 2004173853 A | 6/2004 |
| JP | 2005103257 A | 4/2005 |
| WO | 9521644 A1 | 1/1995 |
| WO | 95/21644 A1 | 8/1995 |
| WO | 2008/065472 A1 | 6/2008 |

* cited by examiner

CLOT TRAP, EXTERNAL FUNCTIONAL MEANS, BLOOD CIRCUIT AND TREATMENT APPARATUS

CROSS REFERENCE TO RELATED APPLICATIONS

This application claims the benefit of U.S. Provisional Application No. 61/185,623 filed Jun. 10, 2009, and claims priority to German Patent Application No. 10 2009 024 495.6 filed Jun. 10, 2009 and German Patent Application No. 10 2009018 664.6 filed Apr. 23, 2009, all of which are herein incorporated by reference in their entirety.

FIELD OF INVENTION

The present invention relates to a clot trap. It further relates to an external functional means, a blood circuit, as well as a treatment apparatus.

SUMMARY OF THE INVENTION

Clot traps are employed i. a. in extracorporeal blood circuits in order to trap or retain clots or thrombi present in the extracorporeal blood stream. It is an object of the present invention to specify a further clot trap.

The clot trap of the invention comprises a screen surface, or clot trap surface, suited and intended for collecting clots of a fluid flowing through the screen surface.

The expression "screen surface" as presently used designates a means or component of the clot trap that is intended to prevent a passage of the clot through the clot trap.

In a preferred manner, the screen surface is a means having a mechanically acting screening or filtering effect, without being restricted thereto.

Furthermore, the screen surface may alternatively or additionally be suited and intended for retaining or dissolving clots, for example by physical and/or chemical effects.

In accordance with the invention, the screen surface has a disc-shaped configuration.

The expression "disc-shaped" as presently used means that the screen surface is configured—preferably substantially or entirely—in the shape of a disc.

In the following it should be understood that a fluid flowing through the clot trap enters into the clot trap—completely or in parts thereof—on an inflow side, flows through the screen surface, and exits from the clot trap on an outflow side. In accordance with the invention, clots are to be understood to be, e.g., thrombi, solid impurities, and the like.

The expression "fluid" as presently used encompasses—without being restricted thereto—liquids such as medical liquids, e.g., blood, gases, emulsions, suspensions, dispersions, and the like, as well as combinations thereof.

In every embodiment in accordance with the invention, the disc shape of the screen surface may be uneven and/or undulating, curved, or the like. Alternatively, it may have a planar shape in the sense of being flat or contained in a plane.

The disc shape specifies a structure which is clearly larger in a first dimension (the main extension) than in a direction orthogonal thereto.

Figure 6:
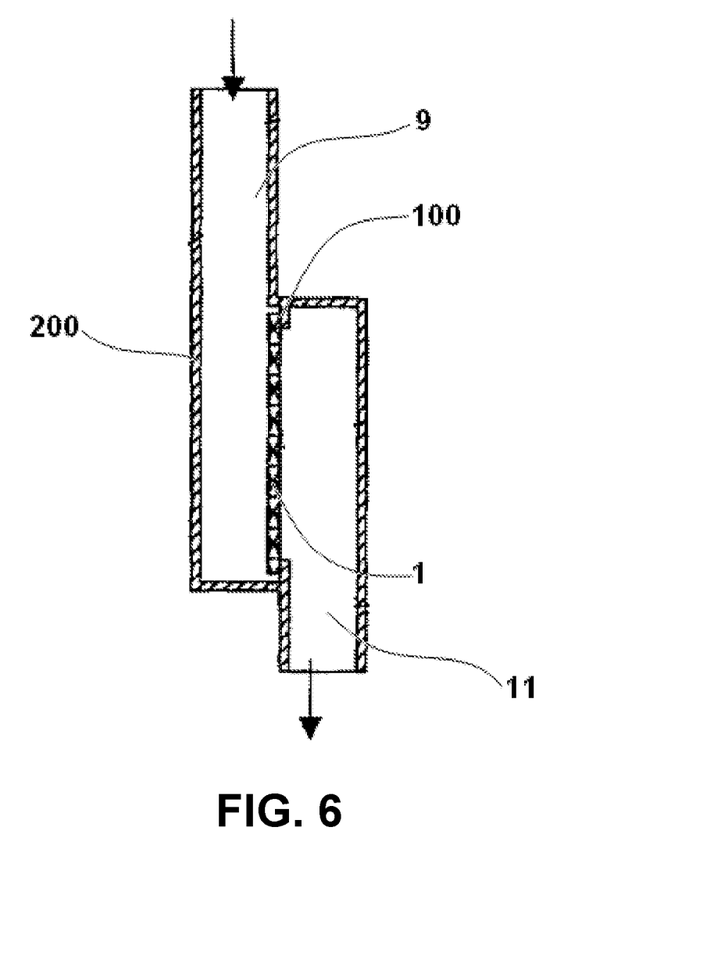
FIG. 6 is a longitudinal sectional view of the clot trap of FIG. 4.

During or for its utilization, the clot trap is arranged substantially vertical, preferably relative to the main extension of the screen surface, as is shown, for example, in FIG. 6.

The expression "substantially vertical" as presently used means that the inclination of the clot trap relative to the vertical may be about 15 degrees at the most in any directions, or that a maximum inclination of +/−15 degrees is particularly preferred. An inclination by less than +/−15 degrees is equally preferred. Such a possibility of inclination by, e.g., 15 degrees in a clockwise direction or by 15 degrees in a counter-clockwise direction to the front or to the rear or to one side (also in any direction) is partly indicated in FIGS. 4 and 7.

The expressions "vertical" and "horizontal" preferably relate to the center of the Earth.

During use, the clot trap may be arranged at a random angle or at a random inclination relative to the center of the Earth.

A chemical filtering or screening effect may be obtained by chemically binding the clots to the screen surface and/or in the screen surface, for example in its pores. The clots may be bound to the screen surface in a reversible or irreversible manner. The clots may be adsorbed on the screen surface by physical effects. The clots may furthermore be dissolved completely or partly at the screen surface.

In a preferred embodiment the screen surface comprises passage openings through which the fluid may flow from the inflow side to the outflow side. With the aid of the passage openings, a mechanical filtering or screening effect may be obtained. The dimensions of the passage openings or a mesh size of the screen surface may be selected such that the clots are retained on the inflow side of the inflowing fluids on account of their size.

The passage openings of the screen surface together form an open total surface area of passage of the screen surface.

The dimensions of the passage openings may be selected such that clots, agglomerations, solid particles, etc. present in the flowing fluid or fluid flow are retained from the fluid flow on the inflow side of the fluid on account of their size and do not reach the outflow side of the clot trap.

Figure 1:
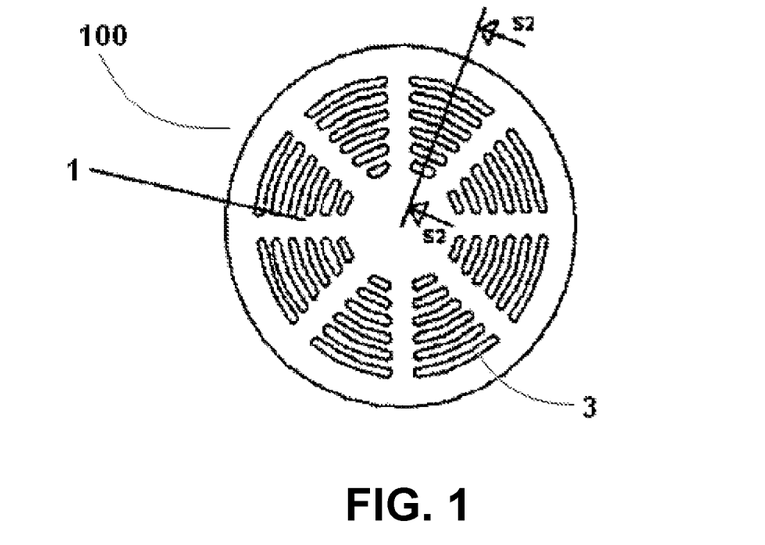
FIG. 1 is a front view, or view from the front, of the clot trap of the invention in accordance with a first embodiment.

In another preferred embodiment, all of the passage openings are arranged on circles or portions of circles, in particular concentric ones. An exemplary arrangement is shown in FIG. 1.

As an alternative, merely a multiplicity of passage openings are arranged on circles, in particular concentric ones.

In a further preferred embodiment, all or only some of the passage openings are arranged radially relative to a center point of the clot trap or the screen surface.

The expression "center point" designates a center point or a point in a central region of the disc-shaped screen surface and/or of the clot trap. This center point may correspond to the center of gravity or geometrical center of gravity of the screen surface and/or of the clot trap and/or to a circle center of a round screen surface and/or of the clot trap.

In comparison with a concentric arrangement of the passage openings, the passage openings in a "radial" arrangement are provided such that they extend from the center point of the screen surface or of the clot trap in a radial direction, in particular in one or several planes that are in parallel with a plane of main extension of the screen surface.

In a preferred embodiment, a number of passage openings is arranged on the entire screen surface.

The passage openings may be arranged so as to be distributed across the screen surface at a respective identical distance from each other. The passage openings may be arranged at an offset from each other, as is shown, for example, in FIG. 2.

The passage openings may be arranged on the screen surface so as to be symmetrical relative to the center point of the screen surface and/or of the clot trap. They may, however, also be arranged asymmetrically on the screen surface.

In a further preferred embodiment, at least one portion of the screen surface does not comprise any passage openings or a smaller number of passage openings in comparison with other regions of the screen surface.

Figure 3:
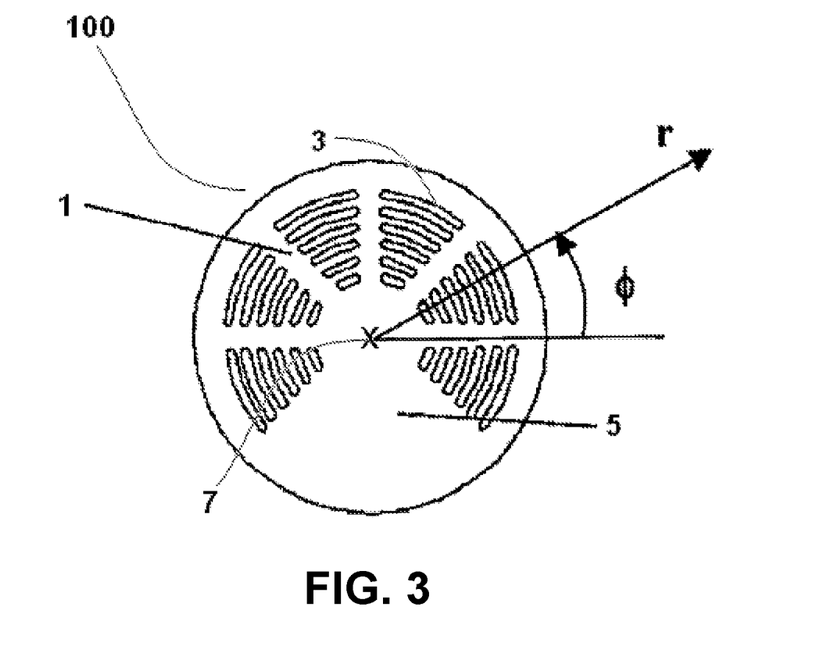
FIG. 3 is a front view of the clot trap of the invention in accordance with a third embodiment.
Figure 4:
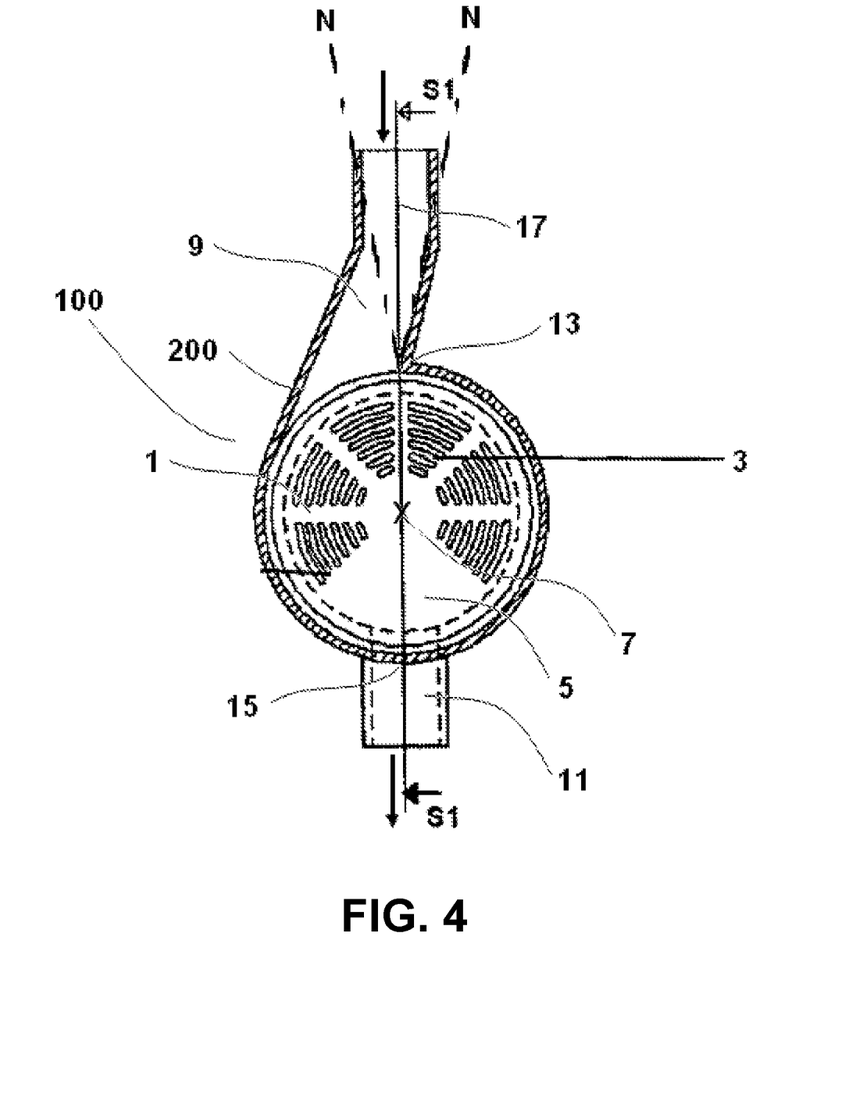
FIG. 4 is a front view of the clot trap of FIG. 3 when arranged in a first housing.

One example of such an arrangement is shown in FIG. 3 and FIG. 4.

The portion having no passage openings or having only comparatively few passage openings may be facing the outflow region of the clot trap or of a housing in which the clot trap is accommodated.

This portion may have the shape of a circle segment. In a preferred manner, in a position of use of the clot trap the circumference of the partial arc of circle is situated downstream from a tip of the partial arc of circle.

The passage opening(s) may have any desired suitable geometric shape. They may, for example, have a polygonal, round and/or elliptical, etc. configuration.

Figure 8:
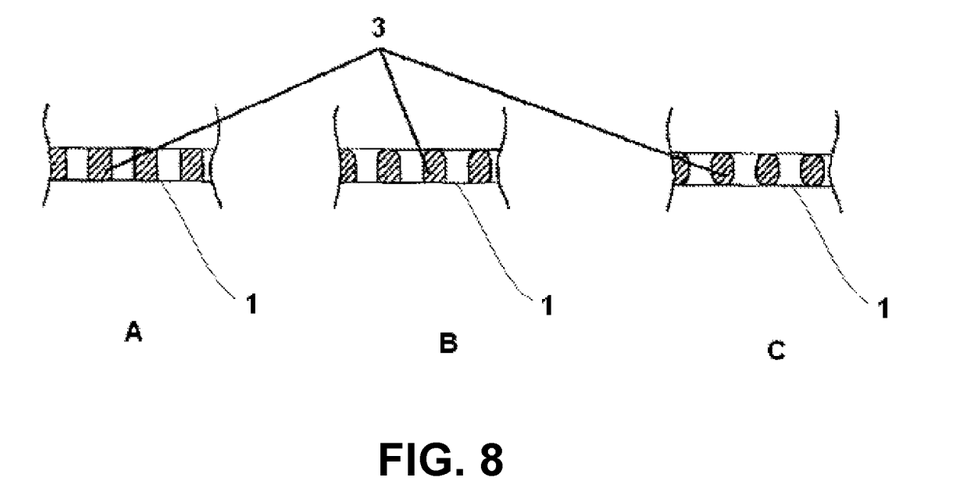
FIGS. 8A-C show embodiments of passage openings of a screen surface.

A number of passage openings may, for example, be designed to have a sharp edge on at least one of the two sides of the screen surface (inflow side and outflow side), as is shown, for example, in FIG. 8A.

As an alternative or in addition, a number of passage openings on at least one side of the screen surface may be designed to be rounded or trimmed. An exemplary embodiment is shown in FIG. 8B.

The passage openings may be designed to be rounded on both sides. An exemplary embodiment is shown in FIG. 8C.

The length and/or the width of the passage openings may, for example, be varied in dependence on the radial distance, or on a distance starting from a central region to the margin or boundary of the screen surface. For instance, the length and/or the width of the passage openings may also increase with an increasing radial distance towards the outside.

The length and/or width of the passage openings may, for example, be varied in dependence on the angular orientation.

An "angle" may be an angle of a circle segment between a straight line through the center point or a point of a central region of the clot trap or of the screen surface and another straight line through the center point of the screen surface along the arc of circle of the clot trap or of the screen surface.

The clot trap may, at least in portions thereof, be made of a hemocompatible base material. The clot trap may be made entirely of a hemocompatible base material.

Examples for suitable hemocompatible base materials include—without being restricted thereto—PVP (polyvinylpyrrolidone) which in a preferred manner is particularly hemocompatible, as well as PP (polypropylene).

In a further preferred embodiment, the clot trap is made of a base material. Suitable base materials include—without being restricted thereto—polypropylene, polyethylene, polycarbonate, polyvinyl chloride (PVC), polyamide (PA), and the like.

The base material is preferably coated with one or several hemocompatible material(s).

The clot trap may be an injection-molded component or an injection-molded element.

The screen surface may be a wire gauze or screening fabric. It may be realized substantially or entirely as a grid structure and/or meshed structure. The screen surface be realized or made of filtering paper, filtering nonwoven, or the like.

The screen surface or the clot trap may be supported or carried by a supporting construction such as a housing, a grid, or the like. A supporting construction may equally have a screening or filtering effect.

For instance, a supporting grid may be provided at or on each side of the screen surface.

In a further preferred embodiment, the clot trap is arranged inside a housing.

A housing may serve as a protection of the clot trap or of the screen surface and/or may serve for fastening these to other structures.

In a preferred embodiment the clot trap is connected to the housing.

The clot trap may be connected to the housing in a releasable manner. It may, for example, be snapped or latched, etc. to the housing.

As an alternative, the clot trap may also be connected to the housing in a non-releasable manner. It may, for example, be welded or bonded, etc. to the housing.

The ratio between open total surface area of passage and total surface area of the screen surface or total surface area of the clot trap may be varied prior to use of the clot trap.

For instance, the ratio between open total surface area of passage and total surface area of the screen surface or total surface area of the clot trap may be varied by realizing or forming passage openings of various or different sizes, in a given case of different shapes, and/or realizing or arranging or providing the portion without passage openings or by varying the size and/or shape thereof.

The clot trap may be integrated in a housing such that it and/or its screen surface separate(s) the inflow region of the housing from the outflow area.

In another preferred embodiment, the clot trap comprises a cover means in at least one portion of an upper side thereof.

Figure 7:
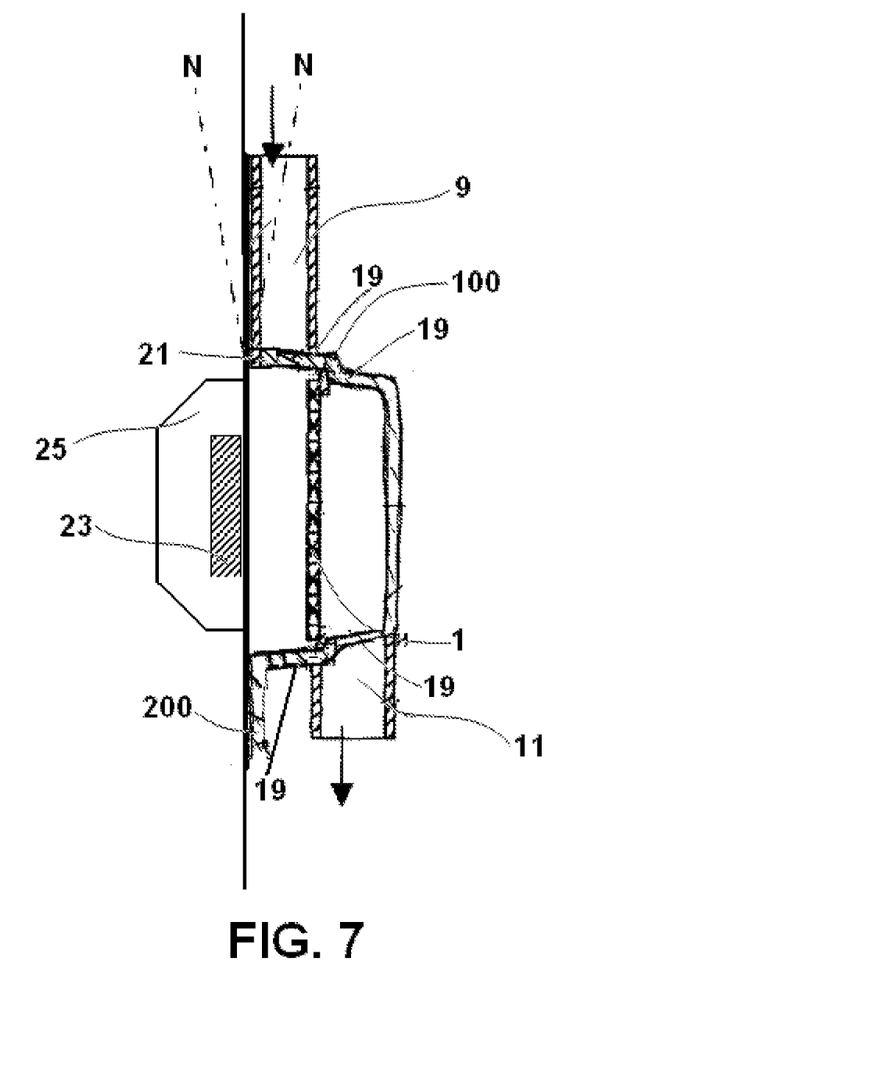
FIG. 7 is a longitudinal sectional view of the clot trap of the invention which is coupled to a sensor.

The cover means may serve as a coupling surface for at least one sensor as is illustrated, for example, in FIG. 7. It may be prepared for this purpose. It may comprise corresponding means for receiving the sensor or a connector equipped therewith, such as clamps, clip means and/or the like.

The object of the invention is also achieved through an external functional means. All the advantages of the clot trap of the invention may also be achieved in an undiminished manner with the external functional means of the invention.

An external functional means of the invention comprises at least one clot trap of the invention.

An "external functional means" may be a single-use component or a single-use article. It may be made of a plastic material.

The external functional means of the invention may be envisioned for use in a treatment method. Treatment methods within the meaning of the present invention encompass medical or medical-technical treatment methods as well as treatment methods of laboratory technology.

In a preferred embodiment, the external functional means of the invention is configured as a blood cassette.

A blood cassette within the meaning of the present invention is, for example, described in German Patent Application No. 10 2009 018 664.6 (representative's file FM19A27) and German Patent Application No. 10 2009 024 468.9. (representative's file FM19B27) filed with the German Patent and Trademark Office on Apr. 23, 2009 and on Jun. 10, 2009 by the applicant of the present invention, respectively, each having the title "*Externe Funktionseinrichtung, Blutbehandlungsvorrichtung zum Aufnehmen einer erfindungsgemäßen externen Funktionseinrichtung, sowie Verfahren*" [External functional means, blood treatment apparatus for receiving an external functional means in accordance with the invention, and method], the respective disclosures of which are herewith fully incorporated by way of reference.

The object of the invention is equally achieved through a blood circuit in accordance with the invention. All the advantages of the clot trap of the invention may also be achieved in an undiminished manner with the blood circuit of the invention.

A blood circuit in accordance with the invention comprises at least one clot trap in accordance with the invention.

The expression "blood circuit" as used within the present specification designates a tubing system which, having the form of an extracorporeal blood circuit, is suited for the treatment of blood.

Both the external functional means and the blood circuit may be provided for use in or on a treatment apparatus.

The object of the invention is equally achieved through a treatment apparatus in accordance with the invention. All the advantages of the clot trap of the invention may also be achieved in an undiminished manner with the treatment apparatus of the invention.

A treatment apparatus in accordance with the invention comprises at least one clot trap of the invention and/or at least one external functional means of the invention and/or at least one blood circuit of the invention.

For instance, the treatment apparatus may be a blood treatment apparatus such as a dialyzing apparatus for performing a dialysis treatment such as hemodialysis, hemofiltration, hemodiafiltration, and the like.

In comparison with conventional clot traps in which the active screen surface has a cylindrical or conical configuration, the flow management achievable by means of the clot trap of the invention advantageously allows to even further prevent clogging of the clot trap or of the screen surface thereof, respectively.

The disc-shaped configuration further allows a space-saving installation of the screen surface inside the clot trap in comparison, for example, with the conventional cylindrical clot traps mentioned at the outset.

The disc-shaped configuration may furthermore advantageously contribute to the possibility of realizing, e.g., a blood cassette or a blood tube or the like adapted for installation of the clot trap of the invention which only requires a small structural space.

In particular, if the clot trap of the invention is realized to comprise a partial region without passage openings or with only few passage openings, an obstruction of the outflow region on the rear side of the clot trap in the event of a potential growth of a clot stopped by means of a clot trap may advantageously be slowed.

In addition, by varying length and width of the passage openings and/or by varying the ratio between open total surface area of passage and total surface area of the screen surface or total surface area of the clot trap, a flow through the passage openings may advantageously be altered and optimized such that an optimum flow through the clot trap is obtained. To this end, it is also advantageously possible to optimize the total surface area of passage of the passage openings. An optimized flow passage may result in improved rheological conditions and favorably influence, i. a., a further growth of clots at the clot trap.

A round configuration of the passage openings may advantageously contribute to substantially reducing or preventing a flow delamination or interruptions of fluids passing through the passage openings.

In this way it may advantageously be possible to reduce hemolysis and/or a blood clotting activation.

The housing to which the clot trap of the invention is fastened may advantageously be configured such that air bubbles present on the inflow side of the fluid flow may rise up. The air bubbles may thus advantageously leave the inflow region of the clot trap. This is in particular advantageously possible whenever the screen surface of the clot trap is configured with sufficient elevation relative to a horizontal line. To this end, it may be inclined, e.g., at 45 to 90 degrees. In a preferred manner it is arranged vertically.

In particular constructions, a vertical or substantially vertical arrangement of the screen surface may moreover contribute to saving space in comparison with a horizontal arrangement. This is in particular true if the vertically arranged screen surface is arranged in parallel or substantially in parallel with a cover (such as a film) of a blood cassette in which it is integrated. As an example of such a blood cassette, mention is again made of the one named in the foregoing.

The inflow to the clot trap may advantageously take place in such a manner that the inflow side is rinsed as thoroughly as possible. For instance, this may advantageously be achieved with an inflow as tangential as possible.

Figure 5A:
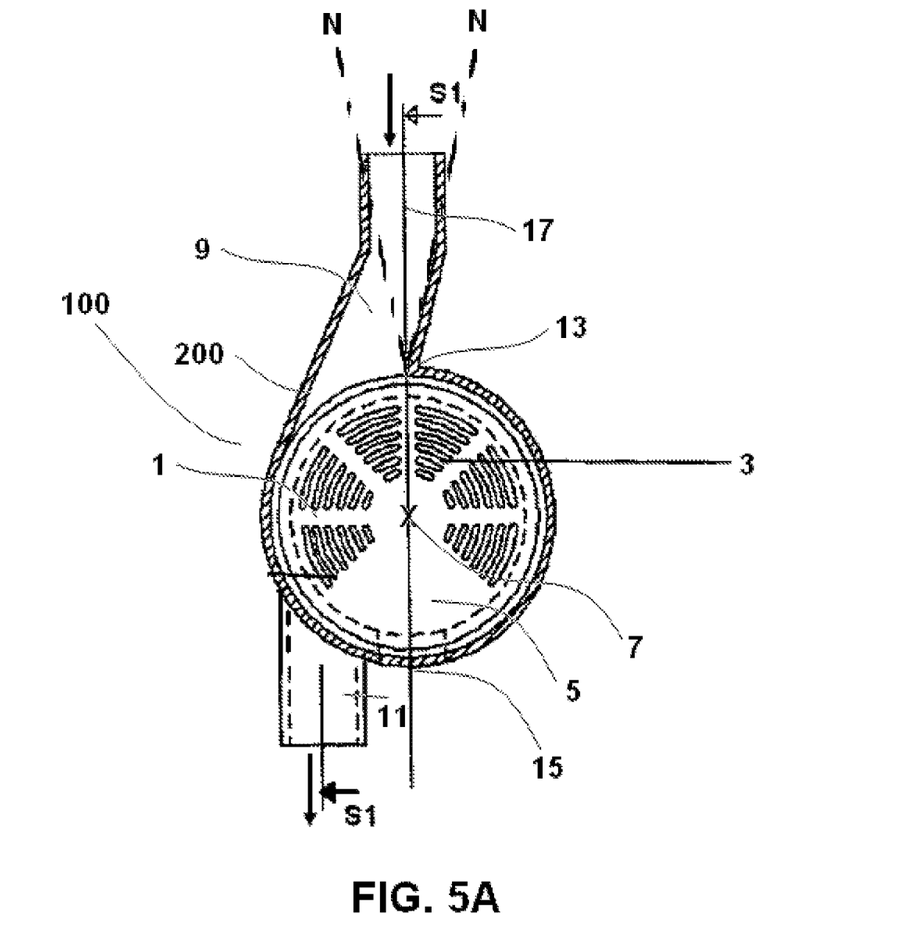
FIG. 5A is a front view of the clot trap of the invention of FIG. 2 in a second housing.
Figure 5B:
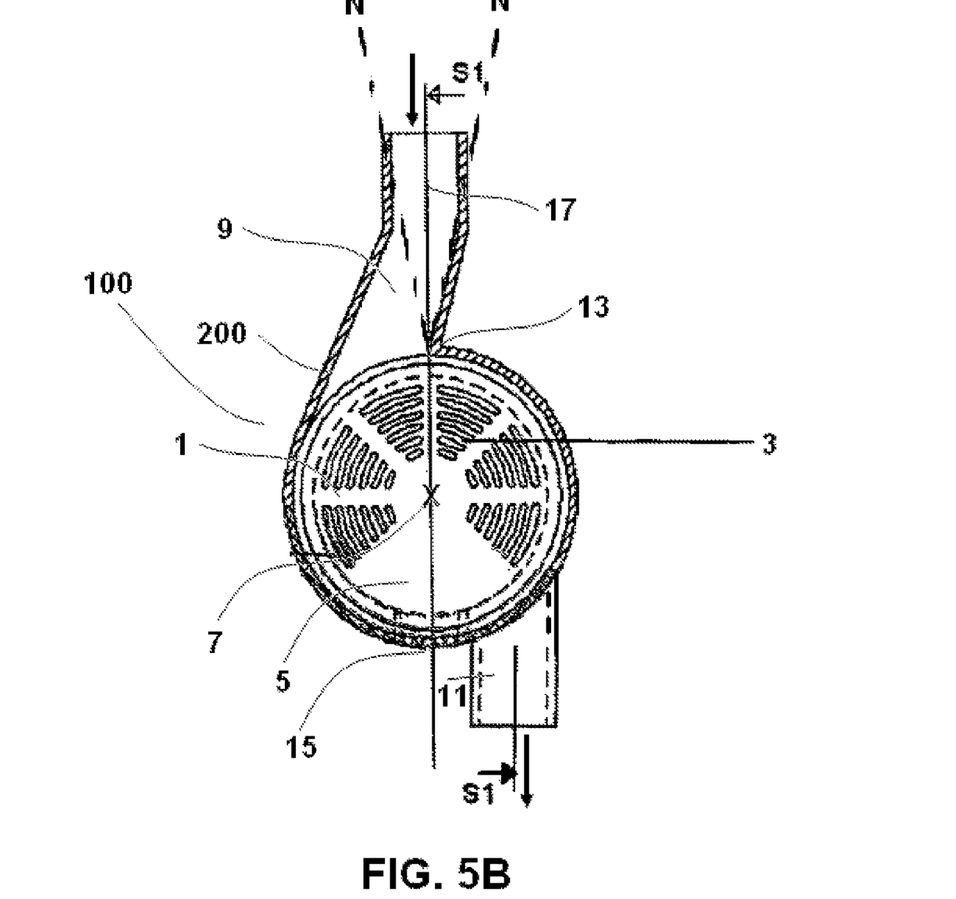
FIG. 5B is a front view of the clot trap of the invention of FIG. 2 in a third housing.

"Tangential" may herein mean a flow impinging on the clot trap substantially in a plane in parallel with the plane of main extension of the screen surface. Tangential may be understood as is visible in FIGS. 4, 5A and 5B and 6. Likewise, as is shown in FIGS. 5A and 5B, the outflow may also take place tangentially or laterally or in a marginal area of the housing or non-centrally.

Additionally, by arranging the passage openings on concentric (partial) circles it may advantageously be achieved that a rotational movement of the fluids—particularly in the event of tangential entry or inflow—will also continue to the outflow side and thus may further improve rinsing of the outflow side.

The present clot trap may thus advantageously be suited to counteract the formation of blood clots—in the sense of Virchow's triad—in the manner of a single action or multiple actions.

BRIEF DESCRIPTION OF THE DRAWINGS

In the following, the present invention shall be described by making reference to the appended drawings. In the drawings, identical reference numerals designate same or identical elements, wherein.

DETAILED DESCRIPTION OF THE DRAWINGS

FIG. 1 shows a clot trap 100 of the invention in accordance with a first embodiment having a screen surface 1 in a front view. In the screen surface 1, passage openings 3 are arranged on concentric partial circles.

Figure 2:
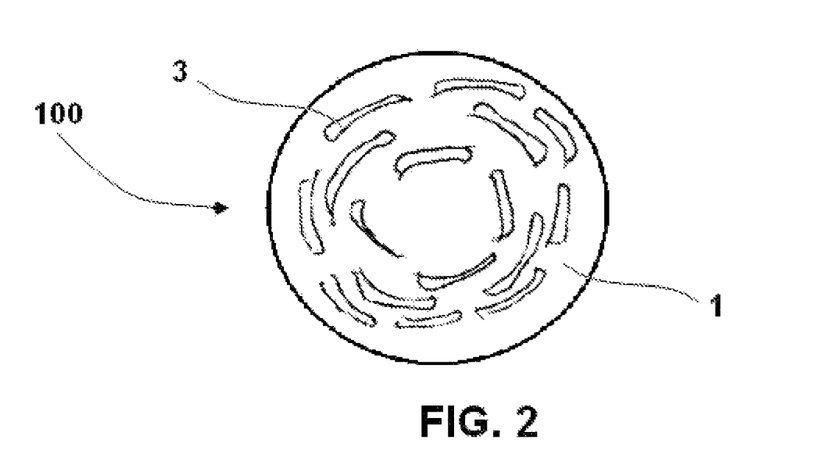
FIG. 2 is a front view, or view from the front, of the clot trap in accordance with a second embodiment.

FIG. 2 shows the clot trap 100 of the invention in accordance with a second embodiment, in the screen surface 1 of which the passage openings 3 are provided at an offset from each other on circles—possibly also partial circles. Such offset may result in overlapping in a radial direction. This is, however, not required.

FIG. 3 shows a clot trap 100 in accordance with a third embodiment. The clot trap 100 comprises passage openings 3 in the screen surface 1 which are situated on concentrically arranged partial circles. The partial circles subdivide the screen surface 1 into segments. The passage openings 3 are also arranged in segments. In a portion 5 no passage openings are provided.

The length of the passage openings 3 changes, as in FIG. 1, depending on the radial distance r of the passage openings 3 from a center point 7 of the screen surface 1. The length of the passage openings 3 changes in a circumferential direction of the screen surface 1 depending on the angular orientation φ of the passage openings 3 from a center point 7 of the screen surface 1.

FIG. 4 shows a front view of the clot trap 100 of FIG. 3 which is here arranged in a first housing 200.

In an inflow region 9 of the housing 200 a tangential arriving flow—i.e., a flow directed to a marginal area or to a circumference (not to be understood as an end side) of the screen surface 1—of a fluid is provided. The fluid flow or the direction of flow thereof are here and in the following indicated by arrows.

The fluid or fluid flow enters into the clot trap 100 through the inflow region 9 and exits from the clot trap 100 at an outflow region 11. The fluid generally enters into the clot trap at the highest point 13 and exits from the clot trap 100 at the lowest point 15. The positional indications of "highest" point 13 and "lowest" point 15 preferably refer to an orientation of the clot trap 100 during its use.

As is indicated by the dashed lines N (inclination), an inclination of the clot trap 100 of the invention during or for its use by—preferably—up to about 15 degrees relative to a vertical or a vertical line toward the center of the Earth or relative to the drawing, is admissible.

FIG. 5A shows a front view, or view from the front, of the clot trap 100 of the invention in a second housing 200. In difference from the first housing 200 as shown, e.g., in FIG. 4, the outflow region 11 in FIG. 5A is arranged at an offset to the left relative to a center axis 17, i.e., an axis through the center point 7 of the clot trap. The outflow is tangential.

FIG. 5B shows a front view of the clot trap 100 of the invention in a third housing 200. In difference from the representation in FIG. 5A or in FIG. 4, the outflow region 11—relative to the representation in FIG. 5B—is arranged at an offset to the right relative to the center axis 17. In the fifth embodiment, too, a tangential outflow of the fluid passing through the clot trap 100 is provided.

FIG. 6 shows a sagittal or longitudinal sectional view along S1-S1 of FIG. 4 through the center point 7. As is shown in FIG. 4, the line S1-S1 corresponds to the center axis 17 through a center of the clot trap 1. The clot trap 100 is arranged vertically in the housing 200. The portion 5 without passage openings is located at the bottom in FIG. 6 while facing or being adjacent to the outflow region 11.

FIG. 7 shows a longitudinal sectional view of the clot trap 100 of the invention inside a housing 200 in turn having a different configuration. As is shown in FIG. 7, the housing 200 comprises steps or oblique portions 19.

The clot trap 100 is provided with a cover means, e.g., a film 21. The film 21 may serve as a coupling surface for a sensor 23 above the clot trap 100. The sensor 23 may be a pressure sensor. By means of the sensor 23 it is, for example, possible to measure a pressure of a fluid present in the inflow region 9 of the clot trap 100. Through the intermediary of a connector 25 the sensor 23 is connected, for example, to a treatment apparatus (not shown) or a control or regulating means (not shown) thereof.

In FIG. 7, too, the dashed lines N (inclination) indicate that the clot trap 100 of the invention may be inclined during or for its use by—preferably—up to about 15 degrees relative to a vertical or a line perpendicular to the center point.

FIGS. 8A to 8C show possible embodiments of passage openings 3 of the screen surface 1. FIGS. 8A-C show configurations of the passage openings 3 along a section S2-S2 through the screen surface 1 in accordance with FIG. 1. The passage openings 3 in FIG. 8A are realized with sharp edges. The passage openings 3 in FIG. 8B are made round on one side (at the top in FIG. 5B). In FIG. 8C the passage openings 3 are made round on both sides.

| List of Reference Numerals | |
|---|---|
| Reference Numeral | Description |
| 100 | clot trap |
| 200 | housing |
| 1 | screen surface |
| 3 | passage openings |
| 5 | portion without passage openings |
| 7 | center point of the screen surface |
| 9 | inflow region |
| 11 | outflow region |
| 13 | highest point of the clot trap |
| 15 | lowest point of the clot trap |
| 17 | center axis |
| 19 | oblique portion(s) |
| 21 | film |
| 23 | sensor |
| 25 | connector |
| N | inclination |

We claim:

1. A blood cassette comprising:
   a clot trap including a screen surface for collecting clots in a blood flowing through the screen surface, the screen surface configured in the shape of a disc; and
   a cover means;
   wherein the screen surface is arranged such that an inflow of the blood is directed in a tangential direction substantially parallel to a main plane of extension of the screen surface;
   wherein the screen surface is substantially parallel to the cover means,
   wherein the blood enters into the clot trap through an inflow region and exits from the clot trap at an outflow region, the inflow region and the outflow region disposed on opposite sides of the clot trap,
   wherein the screen surface comprises at least one first portion having a plurality of segments of passage openings and at least one second portion without passage openings, wherein the at least one first portion at least one of faces or is adjacent to the inflow region, and the at least one second portion at least one of faces or is adjacent to the outflow region, wherein a distance between adjacent segments of the plurality of segments is smaller than a distance defining the at least one second portion.

2. A blood circuit comprising at least one blood cassette according to claim 1.

3. A treatment apparatus comprising:
   the blood cassette according to claim 1; and
   a blood circuit.

4. The treatment apparatus of claim 3, wherein the treatment apparatus is a blood treatment apparatus.

5. The blood cassette according to claim 1, wherein the screen surface is arranged such that an outflow of the blood is directed in a tangential direction substantially parallel to a main plane of extension of the screen surface.

6. The blood cassette according to claim 1, wherein the passage openings are configured to allow the blood to flow therethrough.

7. The blood cassette according to claim 1, wherein a number of passage openings are arranged in concentric circles or partial circles on the clot trap.

8. The blood cassette according to claim 1, wherein a number of passage openings are arranged radially relative to a center point of the clot trap or of the screen surface.

9. The blood cassette according to claim 1, wherein a number of passage openings are arranged on the entire screen surface.

10. The blood cassette according to claim 1, wherein the at least one second portion of the screen surface that does not comprise any passage openings faces a housing in which the clot trap is adapted to be accommodated.

11. The blood cassette according to claim 6, wherein a number of passage openings on one of two sides of the screen surface are designed to have sharp edges.

12. The blood cassette according to claim 6, wherein a number of passage openings are designed to be rounded on one side of the screen surface.

13. The blood cassette according to claim 6, wherein a number of passage openings are designed to be rounded on both sides.

14. The blood cassette according to claim 1, wherein the clot trap is manufactured of at least one hemocompatible base material.

15. The blood cassette according to claim 1, wherein the clot trap is coated with at least one hemocompatible material.

16. The blood cassette according to claim 1, further comprising:
a housing wherein the clot trap is arranged in the housing.

17. The blood cassette according to claim 16, wherein the clot trap is connected to the housing.

18. The blood cassette according to claim 16, wherein the clot trap is snapped to the housing.

19. The blood cassette according to claim 16, wherein the clot trap is welded to the housing.

20. The blood cassette according to claim 1, wherein the cover means serves as a coupling surface for at least one sensor.

* * * * *